United States Patent
Schaffer

(10) Patent No.: US 7,717,901 B2
(45) Date of Patent: May 18, 2010

(54) INSTRUMENT FOR PERFORMING LIPOSUCTION

(76) Inventor: Roland Schaffer, Zollikerstrasse 221, CH-8008 Zürich (CH)

(*) Notice: Subject to any disclaimer, the term of this patent is extended or adjusted under 35 U.S.C. 154(b) by 0 days.

(21) Appl. No.: 10/543,476

(22) PCT Filed: Feb. 4, 2004

(86) PCT No.: PCT/EP2004/000493

§ 371 (c)(1),
(2), (4) Date: Feb. 22, 2006

(87) PCT Pub. No.: WO2004/071311

PCT Pub. Date: Aug. 26, 2004

(65) Prior Publication Data

US 2006/0241567 A1    Oct. 26, 2006

(30) Foreign Application Priority Data

Feb. 11, 2003    (EP) .................................. 03405073

(51) Int. Cl.
*A61M 1/00*    (2006.01)
(52) U.S. Cl. .................... 604/542; 604/540; 604/541
(58) Field of Classification Search .......... 604/19, 604/22, 35, 540–544, 317; 606/167
See application file for complete search history.

(56) References Cited

U.S. PATENT DOCUMENTS

| 4,487,600 | A | * | 12/1984 | Brownlie et al. | .............. 604/35 |
| 5,658,307 | A |   | 8/1997  | Exconde |  |
| 5,725,495 | A | * | 3/1998  | Strukel et al. | .................. 604/44 |
| 5,817,050 | A |   | 10/1998 | Klein |  |
| 5,827,218 | A | * | 10/1998 | Nguyen et al. | ................. 604/30 |
| 5,947,988 | A | * | 9/1999  | Smith | .......................... 606/167 |
| 5,968,008 | A | * | 10/1999 | Grams | .......................... 604/35 |
| 6,464,694 | B1| * | 10/2002 | Massengill | .................. 606/15 |
| 2002/0169469 | A1 |  | 11/2002 | Klein |  |

FOREIGN PATENT DOCUMENTS

BE    1 006 811    12/1994

\* cited by examiner

*Primary Examiner*—Michele Kidwell
(74) *Attorney, Agent, or Firm*—Wenderoth, Lind & Ponack, L.L.P.

(57) ABSTRACT

An instrument for performing liposuction with a longitudinally extended rod-shaped part that, at its rear end, has a handle and a front end piece for partially introducing the rod-shaped part under the skin at a site to be treated. The rod-shaped part is, at least over a portion of its length, provided with a roughened surface. This enables the rod-shaped part to be partially introduced under the skin at the site that has already been treated with a suction instrument. At this location, the rod-shaped part can, with its roughened surface, simultaneously distribute the remaining fatty layer remnants or to remove these remnants from the remaining tissue by means of a to-and-fro movement in the longitudinal direction.

8 Claims, 1 Drawing Sheet

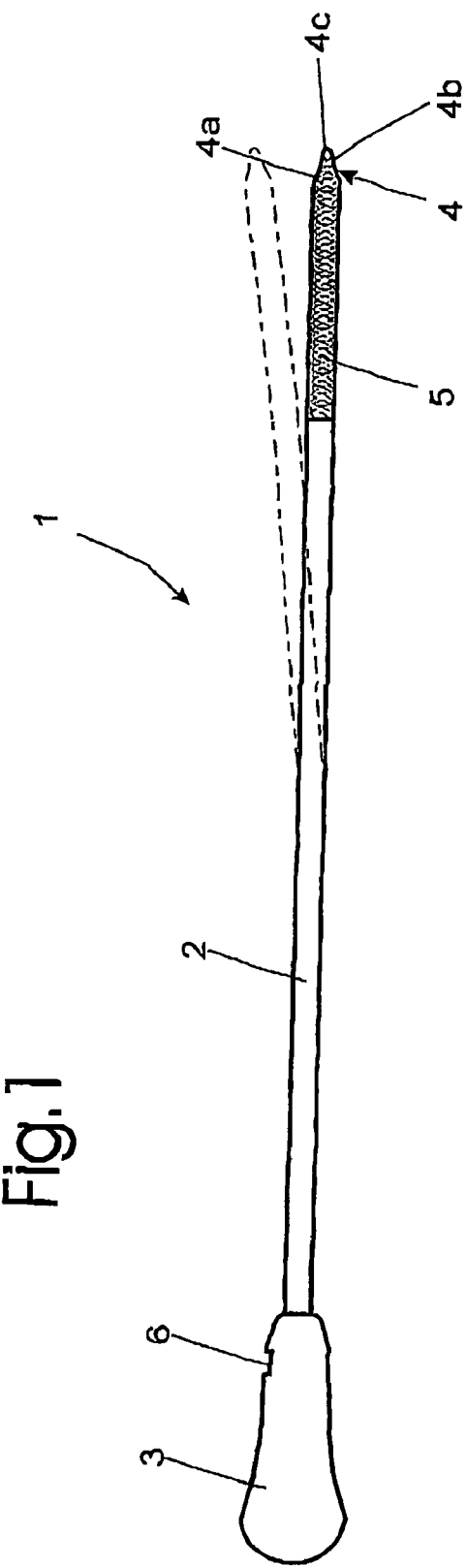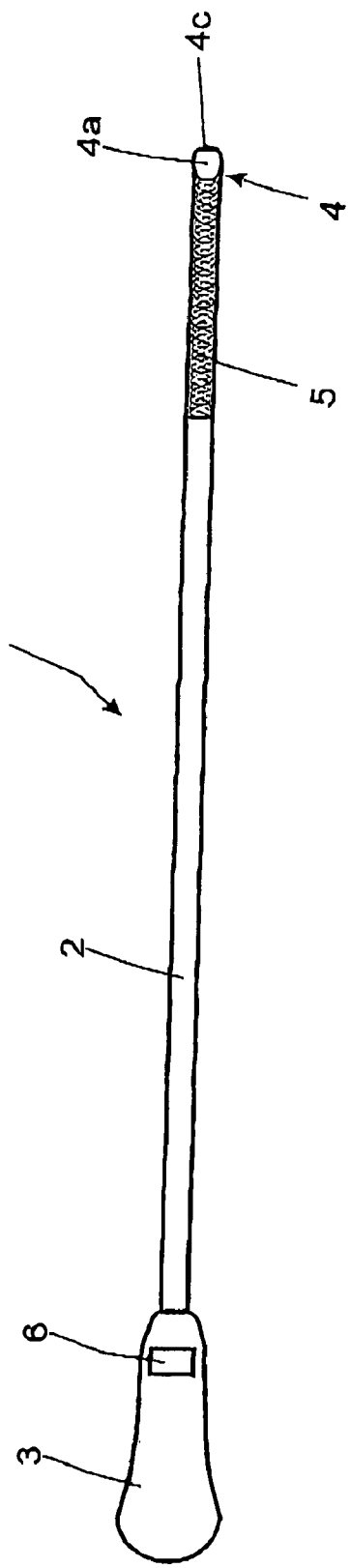

INSTRUMENT FOR PERFORMING LIPOSUCTION

BACKGROUND OF THE INVENTION

1. Field of the Invention

The invention concerns an instrument for performing liposuction with an elongated, rod-like part.

2. Description of the Related Art

Liposuction, i.e., the suctioning of fat is a medical process that is often practised today. A means for carrying out such a process is for example described in EP-B-0 458 989. This means incorporates a suction pipe that can be inserted under the skin into the fat layer that is to be removed. The main problem with this suctioning of fat is that the fat layer is often unevenly removed, whereby the irregularities are then noticeable on the skin surface in a way that is not aesthetically pleasing.

BRIEF SUMMARY OF THE INVENTION

The purpose of this invention is to provide an instrument of the type mentioned above (i.e., instrument for liposuction) which will enable an evening out of irregularities created during fat suctioning, which will in-turn counteract the problem of excess loose skin following liposuction.

This task is solved in accordance with the invention by an instrument where the elongated, rod-like part is equipped with a handle at its rear end, and with a front end for the partial insertion of the rod-like part under the skin to the location that is to be treated, whereby the rod-like part incorporates a roughened surface along at least one part of its length.

Further preferred embodiments of the instrument of this invention form the subject of the dependent claims.

The instrument of this invention can be used alternately together with a suction instrument during liposuction, whereby its elongated, rod-like part is partially inserted under the skin to the location that has already been treated with the suction instrument in order to evenly distribute the remaining fat layer residual with a reciprocal movement of its roughened surface in a longitudinal direction, or to loosen the same from the underlying tissue, so that the same can then once more be removed with the suction instrument. In addition the problem of excess loose skin following liposuction is counteracted in that the skin is tightened by means of mechanical induction of a fine, contracting tissue layer.

With an especially preferred embodiment the rod-like part consists of elastically bendable stainless steel which allows an adjustment of the rod-like part to fit the body parts that are to be treated as well as an especially advantageous, simple handling.

BRIEF DESCRIPTION OF THE DRAWINGS

The invention will now be described in more detail with reference to the drawings, whereby:

FIG. 1 shows a side view of an embodiment of an instrument of the invention; and FIG. 2 shows an overview of the instrument illustrated in FIG. 1.

DETAILED DESCRIPTION OF THE INVENTION

FIGS. 1 and 2 show an instrument 1 to be used for liposuction which incorporates an elongated, rod-like part 2, which is equipped with a handle 3 at its rear end. Preferably, the rod-like part 2 is shaped so as to have a round cross-section, but could for example also have a cross-section incorporating oval or rounded edges. The rod-like part 2 is equipped with an end piece 4 at its front end, incorporating one upper surface 4a as well as one lower surface 4b, which meet to form a front edge 4c. The front edge 4c is rounded in its cross-section (see FIG. 1) as well as its expansion (see FIG. 2).

Whilst the handle 3 is preferably made of plastic the rod-like part 2 is preferably constructed from an elastically bendable stainless steel. Thanks to this elastic bendability the shape of the rod-like part 2 can be changed (by hand), as indicated by the broken line in FIG. 1. In a front area adjoining the front end piece 4 the rod-shaped part 2 incorporates a roughened surface 5 which can for example be produced by cutting or milling (the roughened surface could also extend further towards the back, or several roughened surfaces could be located one behind the other). The end surfaces 4a, 4b are however not roughened (and neither is the edge 4c).

The handle 3 is equipped with a reference surface 6 extending parallel with the front edge 4c of the end piece 4.

The end piece 4 and a part of the rod-shaped part 2 of the instrument 1 of the invention can be inserted under the skin at the location that is to be treated almost parallel with the skin surface and moved backwards and forwards there in a longitudinal direction in order to treat the fat layer with the roughened surface 5 and to separate the same from the underlying tissue. For this the instrument 1 is held in such a way that the front edge 4c (and when part 2 is not bent, also the reference surface 6) extend almost parallel with the skin surface.

During liposuction the instrument 1 is used alternately as an auxiliary to a known suction instrument, whereby the fat layer is normally suctioned off first, and any remaining fat layer residual is removed with the instrument 1 of this invention from the underlying tissue and irregularities rubbed off in a sense, whereafter the fat is once more removed with the suction instrument. Thanks to the shape of the front end piece 4 with its rounded edge 4c, i.e., without sharp edges and corners, skin and tissue damage is prevented.

In theory it would be possible to position a roughened surface, of the instrument for liposuction for removing irregularities created during fat suctioning, directly onto an elongated suction instrument in the form of a hollow rod that can be inserted under the skin.

The invention claimed is:

1. An instrument for performing liposuction on a fat layer located under a surface of skin of a location to be treated, said instrument comprising:
   an elongated rod-shaped part made of elastically bendable stainless steel, having a rounded cross-section, said elongated rod-shaped part including:
   a rear-end portion; and
   a front-end portion having a front-end tip portion which forms a front-end of said instrument, said front-end portion and said front-end tip portion having a roughened surface continuously extending to the front-end of said instrument, said front-end tip portion having (i) rounded side portions formed by said roughened surface which continuously extends to the front-end of said instrument, and (ii) a non-rounded and flat downwardly angled upper surface and a non-rounded and flat upwardly angled lower surface which both extend to meet and form a rounded front edge, said rounded front edge having a rounded cross-section formed by said rounded side portions and said non-rounded and flat upper and lower surfaces, and said rounded front edge extending across a width of said non-rounded and flat upper and lower surfaces and extending between said rounded side portions; and a handle connected to said rear-end portion of said elongated rod-shaped part, wherein said front-end tip portion, said front-end portion, and said roughened surface are operable to be inserted and move backwards and forwards under and along the surface of the skin of the location to be treated so as to treat the fat layer with said roughened surface.

2. The instrument according to claim 1, wherein said handle includes a reference surface positioned to indicate an orientation of said rounded front edge.

3. The instrument according to claim 1, wherein said instrument is operable to be inserted under the skin alternately with a suction instrument.

4. The instrument according to claim 1, wherein said elongated rod-shaped part is formed to have a round, oval, or rounded edge cross-section.

5. The instrument according to claim 2, wherein said elongated rod-shaped part is formed have a round, oval, or rounded edge cross-section.

6. The instrument according to claim 3, wherein said elongated rod-shaped part is formed to have a round, oval, or rounded edge cross-section.

7. The instrument according to claim 1 wherein:
said non-rounded and flat downwardly angled upper surface is a non-roughened surface;
said non-rounded and flat upwardly angled lower surface is a non-roughened surface; and
said rounded front edge is a non-roughened edge.

8. The instrument according to claim 1, wherein said rounded front edge is non-circular.

* * * * *